United States Patent [19]

Hurley et al.

[11] Patent Number: 4,917,670

[45] Date of Patent: Apr. 17, 1990

[54] CONTINUOUS SPINAL ANESTHESIA ADMINISTERING APPARATUS AND METHOD

[76] Inventors: Ronald J. Hurley, 83 Pine St., Norwell, Mass. 02061; Kenneth W. Larson, 57 Liberty La., Keene, N.H. 03431

[21] Appl. No.: 171,895

[22] Filed: Mar. 22, 1988

[51] Int. Cl.$^4$ .............................................. A61M 5/00
[52] U.S. Cl. ...................................... 604/51; 604/164
[58] Field of Search ................ 604/51, 170, 164, 158, 604/778, 256, 282, 280, 264; 128/658, 657, 778

[56] References Cited

U.S. PATENT DOCUMENTS

| | | | |
|---|---|---|---|
| 2,922,420 | 1/1960 | Cheng | 604/158 |
| 3,585,996 | 7/1971 | Reynolds et al. | |
| 3,780,733 | 12/1973 | Martinez-Manzo | 604/158 |
| 3,786,810 | 1/1974 | Pannier et al. | |
| 3,908,635 | 9/1975 | Viek | |
| 3,922,378 | 11/1975 | Kline | 128/772 X |
| 4,068,660 | 1/1978 | Beck | |
| 4,645,491 | 2/1987 | Evans | 604/158 |

OTHER PUBLICATIONS

Bizzarri, et al., Anesthesia and Analgesia 43:393 (1964).
Giuffrida et al., Anesthesia and Analgesia, 51:117 (1972).
Shroff et al., Southern Medical Journal, 81:178 (1988).
Catalog description, "Bizzarri-Giuffrida Set for Continuous Spinal Anesthesia", manufactured by Beckton-Dickinson, 3pp(1983).
Catalog description, "Epidural Catheter and Accessories", Teleflex Medical, 2 pp.
Catalog description, "Arrow-Racz Epidural Catheter", Arrow International Inc., 4 pp.
Hurley, et al., Free Paper Abstract 23, "Continuous Spinal Anesthesia with a Microcatheter Technique", 12th Annual Meeting of American Society of Regional Anesthesia, held Mar. 26-29, 1987.
Hurley, et al., "New Microcatheter Technique Reduces Anesthesia Needs", Anesthesiology News 13(10):12 (Oct. 1987).
H. P. Dean Brit. Med. J. [1907]:869.
W. T. Lemmon, Ann. Surg. 111:141 (1940).
R. A. Hingson et al., Ann. Surg. 118:971 (1943).
E. B. Touhy, Anes. 5:142 (1944).
E. B. Touhy, J.A. M.A. 128:262 (1945).
W. T. Lemmon, Cond. Anes., p. 827 (1946).
R. P. Dripps, N.Y.S.J. Med. 50:1595 (1950).
D. C. Moore, Regional Block, 388.
P. C. Lund, Prince. & Practice of Spinal Anesthesia pp. 377-391.
M. R. Schorr, Anesth. Analg. 45:509 (1966).
J. D. Giuffrida et al., Anesth. Analg. 51:117 (1972).
D. Bizzarri et al., Int. Conc. Ser. 290:376 (1972).
N. Denny et al., Anesth. Analg. 66:791 (1987).
J. D. Giuffrida et al., 9th World Cong. Anesth. Abstracts II: A0902 (1988).

Primary Examiner—Stephen C. Pellegrino
Attorney, Agent, or Firm—David G. Conlin; Henry D. Pahl; Stephan P. Williams

[57] ABSTRACT

A continuous spinal anesthesia administering apparatus is disclosed which comprises a polymeric microcatheter having an external diameter less than about 0.0130 inch (0.330 mm) with a reinforcing stylet therein. A method for administering anesthesia to a patient utilizing this apparatus is also disclosed, as is a catheter kit containing this apparatus.

10 Claims, No Drawings

CONTINUOUS SPINAL ANESTHESIA ADMINISTERING APPARATUS AND METHOD

BACKGROUND OF THE INVENTION

This invention relates to continuous spinal anesthesia and particularly to an improved apparatus through which the anesthesia is administered.

Continuous spinal anesthesia has become a widely recognized technique in the last two decades, having been described by a variety of practitioners including Bizzari et al (*Anesthesia and Analgesia* 43: 393, 1964), Giuffrida et al (*Anesthesia and Analgesia*, 51: 117, 1972), and Shroff et al (*Southern Medical Journal*, 81 : 178 , 1988 ), among others. In the techniques described heretofore, generally a 17 to 21 gauge spinal needle was used to puncture the lumbar due at the desired interspace (L2-3 or L3-4) so as to enter the subarachnoid space, then a flexible catheter (about 20 gauge or 0.81 mm O.D. to about 23 gauge or 0.56 mm O.D.) reinforced with a metal stylet was inserted through the needle, the needle and stylet were withdrawn leaving the catheter in place, and anesthetic was administered through the catheter as required.

Continuous spinal anesthesia as described above has been recognized to provide a number of advantages over single dose injection including accurate control of the level and duration of anesthesia, induction of anesthesia with the patient in the operative position, the use of minimal doses of anesthetic, and the use of short acting anesthetics. In spite of these recognized advantages, however, the continuous technique has not been widely used by practitioners. One apparent reason for this lack of acceptance, among several postulated, is that the incidence of postdural puncture headache is sufficiently high to cause concern.

Postdural puncture headache is primarily attributable to the size of the needle used and incidence of headache decreases as the needle size decreases. Thus, the standard 25 or 26 gauge needle utilized in single injection spinal anesthesia produces a relatively low incidence of headache, while the larger 18 to 20 gauge needle required for continuous spinal anesthesia (the needle must be large enough to allow the catheter to pass through) produces a much greater incidence of headache. This disadvantage has thus prevented greater acceptance of the continuous spinal anesthesia technique.

In U.S. Pat. No. 3,780,733, an effort was made to overcome this disadvantage by coupling a thin 25 gauge needle to the end of a standard 20 gauge catheter and piercing the dura wall, so as to reach the subarachnoid space, only with this small gauge needle. To accomplish this, a larger 15 gauge needle was first partially inserted into the extradural space to act as a guide for the smaller catheter/needle unit. Then, the smaller catheter/needle unit was introduced through the lumen of the larger needle until it penetrated the subarachnoid space with assistance from a stylet inserted in the catheter.

While presumably the apparatus and technique disclosed in the above described patent would achieve a reduction in the incidence of postdural puncture headache, it is believed that the apparatus contemplated would be difficult to manufacture and would raise additional concerns that would detract from its use. One such concern would be the permanence of the coupling connecting the small needle to the catheter. If the needle could be accidentally dislodged while in the patient, the result could be disastrous. A second concern would be the maintenance of a sharp metal needle in the subarachnoid space during surgery. Any unnecessary movement of the needle could cause damage beyond the initial puncture. Neither of these concerns is present if only a flexible, one piece polymeric catheter is inserted in the subarachnoid space.

SUMMARY OF THE INVENTION

The present invention provides a continuous spinal anesthesia administering apparatus which reduces the incidence of postdural puncture headache to an almost negligible level, while avoiding the introduction of any countervailing problems that would detract from its use. The apparatus of the present invention comprises a polymeric microcatheter having an external diameter less than about 0.0120 inch (0.305 mm), so that it will fit through a thin wall 24 to 26 gauge spinal needle, with a reinforcing stylet removably inserted therein. This apparatus may be utilized for the continuous administration of spinal anesthesia to a patient by (1) inserting a hollow surgical needle of about 24 to 26 gauge partially into the desired spinal site, (2) inserting the apparatus of the present invention (i.e. microcatheter with stylet) into said needle and advancing it until it has projected beyond the needle opening and into the desired spinal site (subarachnoid space), (3) withdrawing said needle from the patient while maintaining the catheter in place, (4) withdrawing the stylet from the catheter, and (5) administering anesthetic to the patient through the microcatheter as desired.

DESCRIPTION DESCRIPTION OF THE INVENTION

The continuous spinal anesthesia technique to which this invention applies is one that is currently known in the medical profession and described in detail in the references previously cited in the Background of the Invention, as well as in the references cited therein. In general terms, this technique involves first selecting an appropriate interspinous vertebral space, such as the L2-3 or L3-4 interspace, and inserting a spinal needle until it partially enters the subarachnoid space. A flexible catheter reinforced with a metal stylet is inserted through the needle until the end of the catheter projects beyond the tip of the needle a few centimeters into the subarachnoid space. The needle is then carefully withdrawn from the patient, leaving the catheter in place. Next, the stylet is carefully withdrawn from the catheter. Anesthetic may then be administered through the catheter as required to achieve the desired spinal blockade. As an alternative option, the stylet may be maintained within the microcatheter during infusion of the anesthetic provided that there is sufficient clearance between the stylet and the microcatheter internal wall to allow a sufficient volume of anesthetic to pass through. The anesthetic is generally delivered to the catheter via a syringe connected through an adapter to the catheter.

The present invention provides a substantial improvement in the continuous administration of spinal anesthesia that has not been heretofore possible. This improvement is achieved through the use of a very small gauge spinal needle and a very small gauge microcatheter with reinforcing stylet.

The spinal needle which is utilized in the anesthetic technique of the present invention may be any of those currently available for single dose spinal blockade. The spinal needle will thus be about 24 gauge (0.508 mm O.D.) or smaller with an interior lumen of sufficient size to accept the microcatheter described below. Preferably the spinal needle will be between about 24 gauge and about 26 gauge (0.403 mm O.D.), and most preferably about 25 gauge (0.454 mm O.D.). A thin walled spinal needle, such as the Beckton-Dickinson disposable spinal needle with Quinke point, is particularly advantageous since it has a relatively large lumen through which the microcatheter can be easily inserted. Generally, suitable spinal needles will carry the designation thin wall, extra thin wall or ultra thin wall and such needles are readily available to the medical profession.

A particularly important feature of the present invention is the microcatheter which is employed. This microcatheter is a small gauge, thin-walled microcatheter tube which is capable of being inserted within the previously described small gauge spinal needle and yet it is of sufficient interior diameter so as to provide a sufficient flow rate for proper administration of anesthetic.

This microcatheter can be made of any flexible, nontoxic, biocompatible polymeric material. Such polymeric materials may include, but are not limited to, polyimides, polyamides, polyamide-imides, fluoropolymers, polyurethanes, and polyolefins, as well as such materials containing various fillers to impart desirable properties. The polymeric microcatheter may also contain layers of other biocompatible materials therewithin such as metal or silica as desired to impart particular properties. Thus, the term polymeric should not be strictly interpreted to include only organic homopolymers or copolymers, but rather any material with a polymeric component.

The polymeric microcatheter should have an external diameter less than about 0.0130 inch (0.330 mm), that is, about 29 gauge or smaller. Preferably, the microcatheter will have an external diameter of about 0.0085 inch (0.216 mm or 33 gauge) to about 0.0107 inch (0.272 mm or 31 gauge). The microcatheter should have an internal diameter greater than about 0.0065 inch (0.165 mm) and preferably between about 0.0071 inch (0.180 mm) and about 0.0091 inch (0.230 mm). Most preferably the microcatheter will have an external diameter of about 0.0094 inch (0.238 mm or 32 gauge) and an internal diameter of about 0.0079 inch (0.200 mm). The microcatheter may advantageously contain markings, either visible or radio-opaque, or may itself be radio-opaque to help identify the position of the microcatheter upon insertion into the patient.

A particularly preferred microcatheter for use in the present invention, and one that is currently available and suitable for this use, is a thin walled aromatic polyimide tube manufactured by Hudson Viking Corporation of Trenton, Georgia and Polymicro Technologies Inc. of Pheonix, Ariz. The 32 gauge tube is most preferred.

An important feature of the present invention is the reinforcing stylet, without which it would be difficult or impossible to thread the microcatheter through the spinal needle. The stylet also prevents occlusions in the microcatheter. This stylet must have an outside diameter small enough to enable it to fit within the microcatheter and be easily removed once the microcatheter is in place. Thus, the stylet must have a diameter smaller than the internal diameter of the microcatheter, and preferably less than about 0.0060 inch (0.152 mm).

The stylet, like the microcatheter, must also be nontoxic and biocompatible, in addition to being rigid enough to reinforce the microcatheter so that it can be inserted through the spinal needle. Generally, the stylet will be a metal wire of suitable diameter, preferably made of stainless steel.

It is also particularly important that the stylet have a relatively low coefficient of friction with respect to the microcatheter so that it will slide easily therethrough when being removed. When the microcatheter is fabricated of a material that is not itself inherently slippery (that is, if it is nylon or polyimide, as opposed to polytetrafluoroethylene), then the stylet is preferably coated with a fluoropolymer, or some equivalent material, to give it the required slipperiness. Most preferably, the stylet utilized in the present invention will be a stainless steel wire having an outer diameter of about 0.0025 inch (0.063 mm) to about 0.0035 inch (0.089 mm) with a polytetrafluoroethylene coating of about 0.0010 inch (0.025 mm) to about 0.0020 inch (0.051 mm). Such coated wires are readily available from numerous manufacturers of magnet or motor wires.

In practicing the method of the present invention utilizing the above-described apparatus for the continuous administration of spinal anesthesia, one first inserts the spinal needle (with introducer if desired) into the desired spinal site of the patient (e.g. the L2-3 or L3-4 interspace) until it penetrates the subarachnoid space. Then the apparatus of the present invention, namely the microcatheter with reinforcing stylet, is inserted through the spinal needle and advanced until the inserted end of the microcatheter has projected beyond the needle opening (generally about 2 to 4 cm) into the subarachnoid space. At this point the needle is carefully removed from the patient, then the stylet is removed from the microcatheter, in each case with care to maintain the microcatheter in place. Anesthetic is then administered through the microcatheter as required to achieve and maintain the desired level of spinal blockade.

As an alternative, the anesthetic that may be infused through the microcatheter with the stylet still in place provided that there is sufficient clearance between the stylet and the microcatheter internal walls to allow a sufficient volume of anesthetic to pass through. This is a practical and advantageous alternative when using, for example, a 32 guage microcatheter, with internal diameter of about 0.0079 inch, and a stylet which has an overall outer diameter of about 0.0045 inch (0.003 inch stainless wire with 0.0015 inch PTFE coating). With the stylet maintained in place, the microcatheter will not kink and form an occlusion, and the difficult step of removing the stylet without accidentally moving the position of the microcatheter is avoided.

Generally, the anesthetic is delivered to the microcatheter via a 3cc syringe, although a 1 cc syringe can be utilized to increase the infusion rate. A connector is used to couple the syringe to the microcatheter. It is particularly advantageous to use a Tuohy-Borst adapter as the connecting means. Such an adapter is available from Teleflex Medical Inc. of Jaffrey, N.H. and size 20 to 24 guage is particularly suitable for the apparatus of the present invention.

The apparatus of the present invention may be advantageously made available to the medical profession in the form of a catheter kit which has been packaged in a sterile, sealed package. In addition to the mcrocatheter with inserted stylet, the catheter kit would also advantageously contain a spinal needle of the desired size and a Tuohy-Borst adapter.

While the invention has been described with reference to particular materials and methods, it should be apparent that the substitution of equivalent materials or methods may be equally employed and are contemplated hereunder. For example, the apparatus of the present invention may also be utilized for continuous epidural anesthesia as well as the spinal (or peridural) anesthesia described. The invention is thus defined by the following claims.

What is claimed is:

1. A method for the continuous administration of spinal anesthesia to a patient comprising inserting a hollow surgical needle of about 24 gauge (0.508 mm O.D.) to about 26 gauge, (0.403 mm O.D.) partially into the desired spinal site;

inserting a polymeric microcatheter which is sized to fit within the needle into said needle and advancing it until one end of said microcatheter has projected beyond the needle opening and into the desired spinal site, said microcatheter being reinforced with a reinforcing member which extends substantially the length of the microcatheter;

withdrawing said needle from said patient while maintaining said microcatheter within said spinal site; and administering anesthetic to said patient through said microcatheter without withdrawing the reinforcing member from the microcatheter.

2. The method according to claim 1 wherein said microcatheter has an external diameter less than about 0.0130 inch (0.330 mm).

3. The method according to claim 2 wherein said microcatheter has an external diameter of about 0.0085 inch (0.216 mm) to about 0.0107 inch (0.272 mm).

4. The method according to claim 3 wherein said microcatheter has an internal diameter of about 0.0071 inch (0.180 mm) to about 0.0091 inch (0.230 mm).

5. The method according to claim 4 wherein said reinforcing member comprises a stainless steel wire of about 0.0025 inch (0.063 mm) to about 0.0035 inch (0.089 mm) diameter with a fluoropolymer coating of about 0.0010 inch (0.025 mm) to about 0.0020 inch (0.051 mm) thickness.

6. The method according to claim 5 wherein said microcatheter is connected to an anesthesia injecting means through a connecting means.

7. The method according to claim 6 wherein said connecting means comprises a Tuohy-Borst adapter.

8. The method according to claim 7 wherein said microcatheter is fabricated of an aromatic polyimide.

9. The method of claim 4, wherein said reinforcing member has a diameter of less than about 0.006 inch (0.152 mm).

10. The method of claim 1, wherein said reinforcing member comprises a wire having a diameter of about 0.0025 inch (0.063 mm) to about 0.0035 inch (0.089 mm).

* * * * *

UNITED STATES PATENT AND TRADEMARK OFFICE
CERTIFICATE OF CORRECTION

PATENT NO. : 4,917,670

DATED : April 17, 1990

INVENTOR(S) : Ronald J. Hurley et al.

It is certified that error appears in the above-identified patent and that said Letters Patent is hereby corrected as shown below:

TITLE PAGE: Item No. 76, after "03431" insert --Donald H. Lambert, 92 Whitewood Road, Westwood, MA 02090--

Signed and Sealed this

Twenty-seventh Day of August, 1991

Attest:

HARRY F. MANBECK, JR.

Attesting Officer

Commissioner of Patents and Trademarks